United States Patent
Fasano et al.

(10) Patent No.: US 10,729,733 B2
(45) Date of Patent: *Aug. 4, 2020

(54) PROBIOTICS AND METHODS OF USE

(71) Applicant: H.J. Heinz Company Brands LLC, Pittsburgh, PA (US)

(72) Inventors: Francesca Romana Fasano, Sondrio (IT); Maria Rescigno, Milan (IT)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 47 days.

This patent is subject to a terminal disclaimer.

(21) Appl. No.: 15/989,878

(22) Filed: May 25, 2018

(65) Prior Publication Data

US 2018/0271920 A1    Sep. 27, 2018

Related U.S. Application Data

(63) Continuation of application No. 14/890,026, filed as application No. PCT/US2014/037517 on May 9, 2014, now Pat. No. 9,980,991.

(60) Provisional application No. 61/821,990, filed on May 10, 2013.

(51) Int. Cl.
| A61K 35/747 | (2015.01) |
| C12N 1/20 | (2006.01) |
| A23L 7/10 | (2016.01) |
| A23L 7/104 | (2016.01) |
| A23L 33/00 | (2016.01) |
| A23L 33/135 | (2016.01) |
| A23C 9/123 | (2006.01) |
| A23C 19/032 | (2006.01) |
| C12R 1/225 | (2006.01) |
| A23K 10/18 | (2016.01) |
| A61K 35/741 | (2015.01) |

(52) U.S. Cl.
CPC .......... *A61K 35/747* (2013.01); *A23C 9/1234* (2013.01); *A23C 19/032* (2013.01); *A23K 10/18* (2016.05); *A23L 7/10* (2016.08); *A23L 7/104* (2016.08); *A23L 33/135* (2016.08); *A23L 33/40* (2016.08); *A61K 35/741* (2013.01); *C12N 1/20* (2013.01); *C12R 1/225* (2013.01); *A23V 2002/00* (2013.01); *A23Y 2220/63* (2013.01); *Y02A 50/473* (2018.01)

(58) Field of Classification Search
None
See application file for complete search history.

(56) References Cited

U.S. PATENT DOCUMENTS

| 6,599,504 | B1 | 7/2003 | Wadstrom |
| 6,835,376 | B1 | 12/2004 | Neeser |
| 9,980,991 | B2 | 5/2018 | Fasano |
| 1,003,929 | A1 | 8/2018 | Budelli |
| 1,024,530 | A1 | 4/2019 | Fasano |
| 1,025,140 | A1 | 4/2019 | Budelli |
| 1,025,865 | A1 | 4/2019 | Fasano |
| 2004/0005305 | A1 | 1/2004 | Spivey-Krobath |
| 2006/0018890 | A1 | 1/2006 | Isolauri |
| 2006/0233772 | A1 | 10/2006 | Herz |
| 2007/0042021 | A1 | 2/2007 | Schiffrin |
| 2007/0207132 | A1 | 9/2007 | Speelmans |
| 2007/0274983 | A1 | 11/2007 | Kluijtmans |
| 2008/0199446 | A1 | 8/2008 | Vriesema |
| 2009/0004164 | A1 | 1/2009 | Speelmans |
| 2009/0136643 | A1 | 5/2009 | Bovetto |
| 2009/0186142 | A1 | 7/2009 | Tatewaki et al. |
| 2009/0203592 | A1 | 8/2009 | Beermann |
| 2009/0304655 | A1 | 12/2009 | Donnet-Hughes |
| 2010/0196341 | A1 | 8/2010 | Wei |
| 2010/0278781 | A1 | 11/2010 | Hougee |
| 2011/0028434 | A1 | 2/2011 | Destaillats |
| 2011/0064707 | A1 | 3/2011 | Rochat |
| 2011/0070334 | A1 | 3/2011 | Rangavajla |
| 2011/0293724 | A1 | 12/2011 | Hausch |
| 2011/0293784 | A1 | 12/2011 | Wittke |
| 2012/0014963 | A1 | 1/2012 | Benyacoub |
| 2015/0174199 | A1 | 6/2015 | Fasano |
| 2017/0065648 | A1 | 3/2017 | Fasano |
| 2017/0202231 | A1 | 7/2017 | Budelli |
| 2019/0281846 | A1 | 9/2019 | Budelli |

FOREIGN PATENT DOCUMENTS

| CA | 2761691 | 11/2010 |
| CN | 1350461 | 5/2002 |
| CN | 101451158 | 6/2009 |
| CN | 102021127 | 4/2011 |
| CN | 102046028 | 5/2011 |

(Continued)

OTHER PUBLICATIONS

Adams, Clifford A. "The Probiotic Paradox: Live and Dead Cells Are Biological Response Modifiers." Nutrition Research Reviews, 2010, vol. 23, No. 1, pp. 37-46.

Agostoni, Carlo, et al., "Fermented Infant Formulae Without Live Bacteria." Journal of Pediatric Gastroenterology and Nutrition, 2007, vol. 44, pp. 392-397.

Bar, F., et al., "Cell-free Supernatants of *Escherichia coli* Nissle 1917 Modulate Human Colonic Motility: Evidence from an in Vitro Organ Bath Study." Neurogastroenterol Motil, 2009, vol. 21, pp. 559-566.

Chapat, Ludivine, et al., "Lactobacillus casei Reduces CD8+ T Cell-Mediated Skin Inflammation." European Journal of Immunology, 2004, vol. 34, pp. 2520-2528.

(Continued)

*Primary Examiner* — Michelle F. Paguio Frising
(74) *Attorney, Agent, or Firm* — Fitch, Even, Tabin & Flannery LLP

(57) ABSTRACT

The present invention features methods for treating or reducing the severity of a microbial infection in an infant of a lactating mother. Compositions comprising food products fermented by *Lactobacillus paracasei* CBA L74, International Depository Accession Number LMG P-24778 are administered to a pregnant or lactating mother in order to treat or attenuate the severity of a microbial infection in her offspring.

15 Claims, 3 Drawing Sheets

(56) References Cited

FOREIGN PATENT DOCUMENTS

| | | |
|---|---|---|
| CN | 102065872 | 5/2011 |
| EP | 0130228 | 1/1985 |
| EP | 1364586 | 11/2003 |
| EP | 1723951 | 11/2006 |
| EP | 2452572 | 5/2012 |
| EP | 2452574 | 5/2012 |
| EP | 1565547 | 9/2012 |
| EP | 2510932 | 10/2012 |
| EP | 2648551 | 10/2013 |
| RU | 2134583 | 8/1999 |
| RU | 2205871 | 6/2003 |
| RU | 2243779 | 1/2005 |
| RU | 2385730 | 7/2008 |
| SE | 522747 | 3/2004 |
| WO | 1997049303 | 12/1997 |
| WO | 1999029833 | 6/1999 |
| WO | 2001097822 | 12/2001 |
| WO | 2002018542 | 3/2002 |
| WO | 2002053706 | 7/2002 |
| WO | 2007140622 | 12/2007 |
| WO | 2008003782 | 1/2008 |
| WO | 2008116892 | 10/2008 |
| WO | 2009067000 | 5/2009 |
| WO | 2009144137 | 12/2009 |
| WO | 2009151315 | 12/2009 |
| WO | 2010002244 | 1/2010 |
| WO | 2010008272 | 1/2010 |
| WO | 2010010021 | 1/2010 |
| WO | 2010033424 | 3/2010 |
| WO | 2010034624 | 4/2010 |
| WO | 2010048481 | 4/2010 |
| WO | 2010060722 | 6/2010 |
| WO | 2010066569 | 6/2010 |
| WO | 2010112430 | 10/2010 |
| WO | 2010130661 | 11/2010 |
| WO | 2010130702 | 11/2010 |
| WO | 2010143940 | 12/2010 |
| WO | 2011039328 | 4/2011 |
| WO | 2011110884 | 9/2011 |
| WO | 2011121379 | 10/2011 |
| WO | 2011148221 | 12/2011 |
| WO | 2011149335 | 12/2011 |
| WO | 2012059501 | 5/2012 |
| WO | 2012059502 | 5/2012 |
| WO | 2012062781 | 5/2012 |
| WO | 2012140031 | 10/2012 |
| WO | 2012177556 | 12/2012 |
| WO | 2014183050 | 11/2014 |

OTHER PUBLICATIONS

Chiang, Shen-Shih, et al., "Beneficial Effects of Lactobacillus paracasei subsp. paracasei NTU 101 and Its Fermented Products." Applied Microbiology Biotechnology, 2012, vol. 93, pp. 903-916.
Chinese Office Action, Chinese Application No. 201480026882.7, dated Aug. 9, 2018, 19 pages (with English translation).
D'Arienzo, R., et al., "Distinct Immunomodulatory Properties of Lactobacillus Paracasei Strains." Journal of Applied Microbiology, 2011, vol. 111, pp. 1482-1491.
D'Arienzo, Rossana, et al., "Modulation of the Immune Response by Probiotic Strains in a Mouse Model of Gluten Sensitivity." Cytokine, 2009, vol. 48, pp. 254-259.
De Angelis, Maria, et al., "VSL#3 Probiotic Preparation Has the Capacity to Hydrolyze Gliadin Polypeptides Responsible for Celiac Sprue." Biochimica et Biophysica Acta, 2006, vol. 1762, No. 1, 2006, pp. 80-93.
Di Cagno, Raffaella, et al., "Sourdough Bread Made from Wheat and Nontoxic Flours and Started with Selected Lactobacilli Is Tolerated in Celiac Sprue Patients." Applied and Environmental Microbiology, Feb. 2004, vol. 70, No. 2, pp. 1088-1096.
Di Cagno, Raffaella, et al., "Use of Selected Sourdough Strains of Lactobacillus for Removing Gluten and Enhancing the Nutritional Properties of Gluten-Free Bread." Journal of Food Protection, vol. 71, No. 7, 2008, pp. 1491-1495.
Dong, Honglin, et al., "Comparative Effects of Six Probiotic Strains on Immune Function in vitro." British Journal of Nutrition, 2012, vol. 108, pp. 459-470.
Elias, Peter M., ""Outside-to-Inside" (and Now Back to "Outside") Pathogenic Mechanisms in Atopic Dermatitis." Journal of Investigative Dermatology, May 2008, vol. 128, No. 5, pp. 1067-1070.
European Extended Search Report, European Application No. 14795405. 1, dated Oct. 17, 2016, 7 pages.
Gallo, Marianna. "Formulation of Functional Food Using Constituents Modified by Biochemical and Physical Processes," PhD Dissertation, Universita degli studi di Napoli, Department of Engineering Chemistry, 2009, pp. 1-132.
Gardiner, Gillian E., et al., "A Spray-Dried Culture for Probiotic Cheddar Cheese Manufacture." International Dairy Journal, vol. 12, 2002, pp. 749-756.
Grandy, Giuseppe, et al., "Probiotics in the Treatment of Acute Rotavirus Diarrohoea. A Randomized, Double-Blind, Controlled Trial Using Two Different Probiotic Preparations in Bolivian Children." BMC Infectious Diseases, 2010, vol. 10, pp. 1-7.
Indrio, Flavia, et al., "Effect of a Fermented Formula on Thymus Size and Stool pH in Healthy Term Infants." Pediatric Research, 2007, vol. 62, No. 1, pp. 98-100.
International Patent Application No. PCT/US2014/037517, International Preliminary Report on Patentability and Written Opinion, dated Nov. 10, 2015, 5 pages.
International Patent Application No. PCT/US2014/037517, International Search Report, dated Sep. 11, 2014, 3 pages.
Iversen, Carol, et al., "Cronobacter gen. nov., a new genus to accommodate the biogroups of Enterobacter sakazakii, and proposal of Cronobacter sakazakii gen. nov., Cronobacter malonaticus . . ." International Journal of Systematic and Evolutionary Microbiology, 2008, vol. 58, pp. 1442-1447.
Jimenez, Esther, et al., "Is meconium from healthy newborns actually sterile?" Research in Microbiology, vol. 159, 2008, pp. 187-193.
Kalliomaki, Marko, et al., "Distinct Pattens of Neonatal Gut Microflora in Infants in Whom Atopy Was and Was Not Developing." Journal of Allergy and Clinical Immunology, Jan. 2001, vol. 107, No. 1, pp. 129-134.
Kearney, N., et al., "Development of a Spray Dried Probiotic Yoghurt Containing Lactobacillus Paracasei NFBC 338." International Dairy Journal, 2009, vol. 19, pp. 684-689.
Kirjavainen, P.V., et al., "Aberrant Composition of Gut Microbiota of Allergic Infants: A Target of Bifidobacterial Therapy at Weaning?" Gut, 2002, vol. 51, pp. 51-55.
Kristo, E., et al., "Modelling of Rheological, Microbiological and Acidification Properties of a Fermented Milk Products Containing a Probiotic Strain of Lactobacillus Paracasei." International Dairy Journal, vol. 13, 2003, pp. 517-528.
Lee, Joohee, et al., "Meta-Analysis of Clinical Trials of Probiotics for Prevention and Treatment of Pediatric Atopic Dermatitis." Journal of Allergy and Clinical Immunology, Jan. 2008, vol. 121, No. 1, pp. 116-121.
M'hir, Sana, et al., "Gluten Proteolysis As Alternative Therapy for Celiac Patients: A Mini-Review." African Journal of Biotechnology, Apr. 10, 2012, vo. 11, No. 29, pp. 7323-7330.
Moroi, Miki, et al., "Beneficial Effect of a Diet Containing Heat-Killed Lactobacillus Paracasei K71 on Adult Type Atopic Dermatitis." Journal of Dermatology, 2011, vol. 38, pp. 131-139.
Ortiz-Andrellucchi, Adriana, et al., "Immunomodulatory Effects of the Intake of Fermented Milk with Lactobacillus casei DN114001 in Lactating Mothers and Their Children." British Journal of Nutrition, 2008, vol. 100, pp. 834-845.
Rizzello, Carlo G. et al., "Highly Efficient Gluten Degradation by Lactobacilli and Fungal Proteases during Food Processing: New Perspectives for Celiac Disease." Applied and Environmental Microbiology, Jul. 2007, vol. 73, No. 14, pp. 4499-4507.
Robert, Herve, et al., "Biodiversity of lactic bacteria in French wheat sourdough as determined by molecular characterization using

(56) References Cited

OTHER PUBLICATIONS species-specific PCR." International Journal of Food Microbiology, 2009, vol. 135, No. 1, pp. 53-59.

Russian Office Action, Russian Patent Application No. 2015150082, dated Mar. 5, 2018, 16 pages (with English translation).

Sanz, Yolanda, et al., "Unraveling the Ties Between Celiac Disease and Intestinal Microbiota." International Reviews of Immunology, 2011, vol. 30, pp. 207-218.

Savijoki, Kirsi, et al. "Purification and Molecular Characterization of a Tripeptidase (PepT) from Lactobacillus helveticus." Applied and Environmental Microbiology, Feb. 2000, vol. 66, No. 2, pp. 794-800.

Wagner, R. Doug, et al., "Probiotic Effects of Feeding Heat-Killed Lactobacillus acidophilus and Lactobacillus casei to Candida albicans-Colonized Immunodeficient Mice." Journal of Food Protection, 2000, vol. 63, No. 5, pp. 638-644, Abstract only.

Winkler, Petra, et al., "Molecular and Cellular Basis of Microflora-Host Interactions." The Journal of Nutrition, 2007, vol. 137, pp. 756S-772S.

Zhou, Xiaodan, et al., "Laxative Effect of Lactobacillus paracasei LC-01 on Constipation Mice." Science and Technology of Dairy Industry. 2012, vol. 35, No. 5, pp. 7-11.

Campeotto, Florence, et al., "A Fermented Formula in Pre-Term Infants: Clinical Tolerance, Gut Microbiota, Down-Regulation of Faecal Calprotectin and Up-Regulation of Faecal Secretory IgA." British Journal of Nutrition, 2011, vol. 105, pp. 1843-1851.

Martin-Diana, A.B., et al., "Development of a Fermented Goat's Milk Containing Probiotic Bacteria." International Dairy Journal, 2003, vol. 13, issue 10, pp. 827-833, Abstract only.

Satoh, Yayoi, et al., "Bifidobacteria Prevents Necrotizing Enterocolitis and Infection in Preterm Infants." International Journal of Probiotics and Prebiotics, 2007, vol. 2, No. 2/3, pp. 149-154.

Wang, N.-F., et al., "Evaluation of Peanut Flour Fermented with Lactic Acid Bacteria as a Probiotic Food." Food Science and Technology International, 2007, vol. 13, No. 6, pp. 469-475.

PROBIOTICS AND METHODS OF USE

CROSS-REFERENCE TO RELATED APPLICATIONS

This application is a continuation of U.S. application Ser. No. 14/890,026, filed Nov. 9, 2015, now U.S. Pat. No. 9,980,991, which is a national phase application of International Application No. PCT/US2014/037517, filed May 9, 2014, which claims the benefit of U.S. Provisional Application No. 61/821,990, filed on May 10, 2013, which are hereby incorporated by reference in their entireties.

FIELD OF THE INVENTION

The present invention relates to compositions comprising probiotic organisms and methods of administering those compositions to pregnant and lactating subjects. The methods are useful for the treatment of infection in the offspring such subjects.

BACKGROUND OF THE INVENTION

Despite modern clinical advances, infections continue to cause significant neonatal morbidity and mortality, especially in small preterm neonates. According to the World Health Organization, infections, including sepsis, pneumonia, tetanus and diarrhea, account for about 36% of the 3.3 million neonatal deaths worldwide per year. The neonatal immune system is functionally immature. Diagnosis of infections in the neonate can be challenging because the symptoms can be subtle and non-specific. Although many infections respond well to antibiotics, delay in antibiotic therapies can lead to rapid progression of infections and the development of very serious conditions such as neonatal sepsis. Untreated neonatal sepsis is invariably fatal. Mortality rates for sepsis in antibiotic-treated infants range between 5% and 60% with the highest rates reported by the lowest income countries. There is a continuing need for new strategies and agents for the treatment and prevention of infections in infants.

SUMMARY OF THE INVENTION

The present invention provides methods of treating a microbial infection in the infant of a lactating mother, the method comprising administering an effective amount of a composition comprising a food product to the mother, wherein the food product has been fermented by the probiotic bacterium, *Lactobacillus paracasei* CBA L74, International Depository Accession Number LMG P-24778. The bacterium can be non-replicating. The composition can be administered prenatally, postnatally or prenatally and postnatally up until the infant is weaned. The method can further include the step of identifying an infant in need of treatment. The microbe can be *Salmonella typhimurium, Cronobacter sakazakii, Escherichia coli, Listeria monocytogenes, Streptococcus pneumoniae Neisseria meningitidis* or a rotavirus. The fermented food product can be a dairy or a cereal product. Also provided are methods of preventing or reducing the severity of a microbial infection in the infant of a lactating mother, the method comprising administering an effective amount of a composition comprising a food product to the mother, wherein the food product has been fermented by the probiotic bacterium, *Lactobacillus paracasei* CBA L74, International Depository Accession Number LMG P-24778. The bacterium can be non-replicating.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENT

Figure 1:
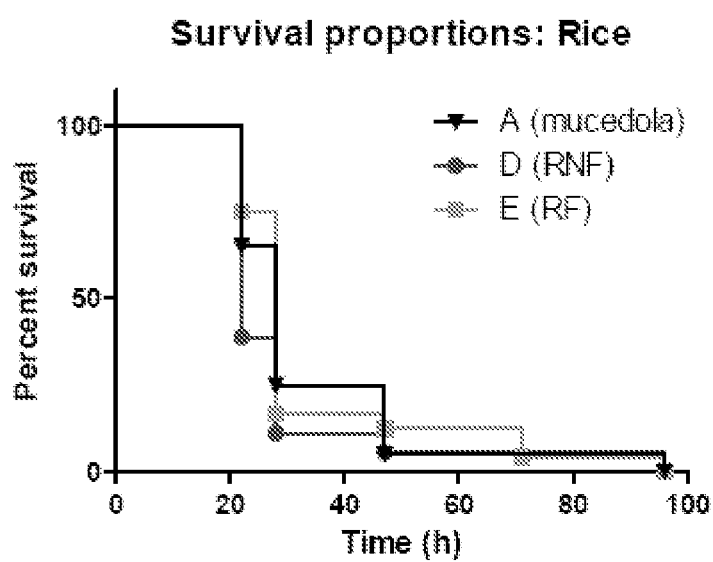
FIG. 1 is a graph depicting the results of an analysis of the effect of maternal administration of *L. paracasei*, strain CBA L74 fermented rice on the survival of *Cronobacter sakazakii* infected offspring.

The present invention is based, in part, on the inventors' discovery that that administration of food fermented by the probiotic organism *Lactobacillus paracasei*, strain CBA L74, to pregnant and lactating animals can reduce or attenuate the severity of microbial infections in their offspring. More specifically, the inventors have found that administration of rice fermented by *L. paracasei*, strain CBA L74 to pregnant and lactating mothers resulted in an increased percentage of survival in their pups following infection with *Cronobacter sakazakii*. Similarly, the inventors also found that administration of milk fermented by *L. paracasei*, strain CBA L74 to pregnant and lactating mothers resulted in an increased percentage of survival in their pups following infection with *Salmonella typhimurium* FB62. Accordingly, the invention features methods for reducing or attenuating the severity of or preventing microbial infections in neonatal organisms by administering compositions comprising food products fermented by *L. paracasei*, strain CBA L74 to their mothers. The compositions can be administered to the mother during the gestation the infant, that is, prenatally. Alternatively or in addition, the compositions can be administered to the mother after the infant is born, that is, postnatally. In some embodiments, the *L. paracasei*, strain CBA L74 is non-replicating.

*Lactobacillus paracasei*, strain CBA L74 was isolated by the inventors and deposited under the Budapest Treaty on the International Recognition of the Deposit of Microorganisms for the Purposes of Patent Procedure on Sep. 9, 2008 at the Belgian Coordinated Collections of Microorganisms (BCCM) Laboratorium voor Microbiologie (LMG), Ghent, Belgium. The Accession Number given by the International Depositary Authority is LMG P-24778. For ease of reading, we will not repeat the phrase "Accession Number LMG P-24778" on every occasion. It is to be understood that where we refer to *L. paracasei*, strain CBA L74, we refer to the deposited strain having the Accession Number LMG P-24778.

While we believe we understand certain events that occur upon administration of compositions comprising or made by fermentation with *L. paracasei* CBA L74, the compositions of the present invention are not limited to those that work by affecting any particular cellular mechanism.

Compositions

L. paracasei CBA L74

The compositions of the invention can include the probiotic organism, L. paracasei CBA L74. The World Health Organization has defined probiotics as: "Live microorganisms which when administered in adequate amounts confer a health benefit on the host." In some embodiments, the L. paracasei CBA L74 can be subjected to treatments that render them non-replicating, for example, exposure to heat, γ-irradiation, or uv-irradiation. A non-replicating L. paracasei CBA L74 can be a dead cell or a living cell that has been rendered incapable of cell division. A non-replicating L. paracasei CBA L74 can be an intact cell or a cell that has undergone partial or complete lysis. In some embodiments, the non-replicating cells can include a mixture of intact and lysed cells.

Food Products

The compositions of the invention can include a physiologically acceptable carrier. The physiological carrier can be a food product or a pharmaceutical carrier. We use the terms "physiologically acceptable" (or "pharmacologically acceptable") to refer to molecular entities and compositions that do not produce an adverse, allergic or other untoward reaction when administered to an animal or a human, as appropriate. Thus, the compositions of the invention include food products fermented by the probiotic organism, L. paracasei CBA L74. The food product may include L. paracasei CBA L74 cells, either live or non-replicating. In some embodiments the food product can be processed to remove all or substantially all the L. paracasei CBA L74 cells. Any food product amenable to fermentation by L. paracasei CBA L74 may be used. The food product can be a dairy product, for example, milk or a milk-based product. Exemplary milk sources include, without limitation, cattle, sheep, goats, yaks, water buffalo, horses, donkeys, reindeer and camels. Regardless of the source, the milk or milk products can be in any form suitable for fermentation by L. paracasei CBA L74. For example, the milk can be whole milk or milk that has been processed to remove some or all of the butterfat, e.g., 2% milk, 1% milk or no-fat milk. Alternatively or in addition, the milk can be previously pasteurized and or homogenized, dried and reconstituted, condensed or evaporated. Fractions of milk products including casein, whey protein or lactose may also be used. In some embodiments, the milk product can be from about 1% to about 30% reconstituted skim milk powder, for example about 2%, about 5%, about 7%, about 9%, about 10%, about 12%, about 15%, about 20%, about 25%, about 30% reconstituted skim milk powder. Prior to fermentation the milk product can be combined with one or more of the following: a) a carbohydrate (e.g., a disaccharide such as dextrose or a starch; b) a lipid; c) a vitamin and d) a mineral. For example, skim milk powder may be combined with dextrose to about 2%, e.g., about 0.25%, about 0.50%, about 0.75%, about 1.0%, about 1.5% or about 2.0%.

The food product can be a cereal product, for example, rice, oats, corn, sorghum, or millet. In some embodiments, the cereal product may be wheat, barley, rye or triticale. The cereal product can be a whole grain or be milled into a flour. The food product can be a single kind of cereal or a mixture of two or more kinds of cereals, e.g., oat flour plus rice flour. The cereal products can be of a grade and type suitable for human consumption or can be products suitable for consumption by domestic animals. Generally, the cereal product is hydrated prior to fermentation. The concentration of cereal can vary, but useful ranges include from about 5% to about 50% weight/volume, for example, about 8% weight/volume, about 10% weight/volume, about 12% weight/volume, about 15% weight/volume, about 18% weight/volume, about 20% weight/volume, about 22% weight/volume, about 25% weight/volume, about 30% weight/volume, about 35% weight/volume, about 40% weight/volume, about 45% weight/volume or about 50% weight/volume. Exemplary concentrations include 15% weight/volume of rice or a mixture of 18.5% weight/volume oat flour plus 5% weight/volume of malted barley flour. The pH of the hydrated cereals may be adjusted using any acid suitable for consumption. The acid can be, for example, an organic acid. Useful organic acids include acetic acid, citric acid, lactic acid, adipic acid, malic acid and tartaric acid. Any combination of two or more acids can be used. In some embodiments, the pH may be adjusted to about 4.0 using citric acid.

The food product can also be a vegetable or a fruit product, for example, a juice, a puree, a concentrate, a paste, a sauce, a pickle or a ketchup. Exemplary vegetables and fruits include, without limitation, squashes, e.g., zucchini, yellow squash, winter squash, pumpkin; potatoes, asparagus, broccoli, Brussels sprouts, beans, e.g., green beans, wax beans, lima beans, fava beans, soy beans, cabbage, carrots, cauliflower, cucumbers, kohlrabi, leeks, scallions, onions, sugar peas, English peas, peppers, turnips, rutabagas, tomatoes, apples, pears, peaches, plums, strawberries, raspberries, blackberries, blueberries, lingonberries, boysenberries, gooseberries, grapes, currants, oranges, lemons, grapefruit, bananas, mangos, kiwi fruit, and caram bola.

The food product can also be a "milk" made from tree nuts or legumes, for example, soymilk or almond milk.

Also contemplated are food products comprising animal proteins, for example, meat, for example, sausages, dried meats, fish and dried fish products.

Regardless of the type of food product that is used, the product is combined with L. paracasei CBA L74 and incubated at a temperature and for a time sufficient for fermentation to occur. Any standard fermentation method known in the art may be used. Specific fermentation conditions will vary according to many factors including, for example, the type of food product, the concentration of the food product, the instrumentation that is used, the sample volume, the initial concentration of the L. paracasei CBA L74 inoculum, the presence, if any, of a co-inoculum, the organoleptic properties of the fermented food, and the intended use of the fermented food.

Both the instrumentation and the substrate (i.e., the food product to be fermented) are sterilized prior to inoculation with L. paracasei CBA L74 in order to decrease the level of, or eliminate, viable bacteria and/or fungi and/or infectious viruses. The instrumentation can be sterilized using standard methods or according to the manufacturer's instructions. Choice of a particular method for sterilization of the substrate will depend, in part, on the stability of the substrate to the sterilization method. For example, the substrate can be sterilized by steam and pressure, e.g. by autoclaving, repeated cycles of heating and cooling (e.g., tyndalization) exposure to high pressures (e.g., pascalization), ultrafiltration, or radiation (e.g., exposure to gamma-, x-, e-beam, and/or ultra-violet (wavelength of 10 nm to 320 nm, e.g., 50 nm to 320 nm, 100 nm to 320 nm, 150 nm to 320 nm, 180 nm to 320 nm, or 200 nm to 300 nm). Aliquots of the substrate can be removed following treatment and plated on suitable media to confirm the absence of bacterial and/or fungal contaminants. If the substrate has been sterilized by exposure to high temperatures, it should be cooled to at least 37° C. prior to inoculation with *L. paracasei* CBA L74.

The substrate can be inoculated with *L. paracasei* CBA L74 according to standard methods, for example, from fresh liquid culture or a freeze-dried culture that has been resuspended in aqueous medium for a short time prior to inoculation. In general, *L. paracasei* CBA L74 are added at concentrations of about $0.5 \times 10^6$ to about $1 \times 10^6$ cfu/ml of substrate, e.g., about $1 \times 10^6$ cfu/ml, about $2 \times 10^6$ cfu/ml, about $5 \times 10^6$ cfu/ml, $7 \times 10^6$ cfu/ml $8 \times 10^6$ cfu/ml. The culture should be agitated sufficiently to produce a relatively uniform distribution of bacteria and substrate, but not excessively since *L. paracasei* CBA L74 is an anaerobic bacterium. For example, a five liter culture may be agitated at about 150 rpm. Fermentation temperature is generally at 37° C. Various parameters, for example, the pH, the partial pressure of $O_2$, stirrer speed, temperature, gas mixing, foam level and substrate concentration can be monitored during fermentation and adjusted accordingly. Growth of the *L. paracasei* CBA L74 can be monitored using standard microbiological methods. Fermentation is carried out until the concentration of *L. paracasei* CBA L74 is about between about 108/ml and about 109/ml. Depending upon the substrate and other conditions, this concentration may be reached in about 10 to about 30 hours after inoculation, e.g., about 12 hours, about 15 hours, about 18 hours, about 24 hours, about 30 hours.

Samples of the substrate can be assayed before, during and after fermentation for quality assurance using standard microbiological methods. Exemplary methods include, but are not limited to, growth on Rogosa agar for *L. paracasei* CBA L74, growth on plate count agar (PCA) for total aerobes, growth on McConkay agar for coliforms, growth on reinforced clostridial agar (RCM) for Clostridia. In addition to colony counts, colony morphologies can be observed and compared to reference samples.

In some embodiments, a co-inoculum can be added along with the *L. paracasei* CBA L74 in order to help initiate fermentation. Useful co-inocula for fermentation of milk products include, for example, without limitation, *Streptococcus thermophilus, Lactobacillus paracasei, Lactobacillus salivarious, Lactobacillus rhamnosus, Lactobacillus casei, Lactobacillus lactis, Lactobacillus delbrueckii*, subsp. *Bulgaricus, Lactobacillus acidophilus, Lactobacillus brevis*, or *Leuconostoc mesenteroides*. In general, the concentration of the co-inoculum will be lower than that of *L. paracasei* CBA L74, for example, about $1 \times 10^4$/ml$\times 10^5$/ml. The final concentration of *S. thermophilus* can range from about $0.5 \times 10^8$/ml to about $2.5 \times 10^8$/ml.

Once suitable concentrations of *L. paracasei* CBA L74 have been reached, the fermented food can be further processed for use. In some embodiments, the fermented food can be fractionated to remove all or substantially all of the *L. paracasei* CBA L74 cells. In some embodiments, the pH of the fermented food can be adjusted, for example from about 3.0 to nearer to neutrality, e.g., 6.5, with the addition of NaOH or KOH. In some embodiments the fermented food can be dried. The fermented food product can be dried by any method known in the art that will result in the retention of immunomodulatory properties of the fermented food. Exemplary drying methods include spray drying, freeze-drying e.g., lyophilization, or drum-drying. The final water content of the fermented food product may vary but can be between about 1% and about 10% or more. In some embodiments, the drying process can render the *L. paracasei* CBA L74 non-replicating.

The dried fermented foods can be hydrated before use. Depending on the amount of liquid used in the hydration, the fermented food products may contain the equivalent of about $10^2$ and $10^{12}$ cfu/ml of *L. paracasei* CBA L74. The dried *L. paracasei* CBA L74 do not form colonies, so it is understood that this amount is calculated based on the number of live bacteria that were present in the fermented foods prior to the drying step. In some embodiments, the fermented food products may include the equivalent of about $10^7$ to about $10^{12}$ cfu/g, e.g., about $5 \times 10^7$ cfu/g, about $1 \times 10^8$ cfu/g, about $5 \times 10^8$ cfu/g, about $1 \times 10^9$ cfu/g, about $5 \times 10^9$ cfu/g, about $1 \times 10^{10}$ cfu/g, about $5 \times 10^{10}$ cfu/g, about $1 \times 10^{11}$ cfu/g, about $5 \times 10^{11}$ cfu/g of dry weight.

Two or more fermented food products prepared by the methods of the invention may be combined prior to administration. For example, fermented milk products may be combined with fermented cereal products. Alternatively, the fermented food product can be combined with other food products, for example, non-fermented food products or food products fermented using other bacterial strains. Any combination can be used provided that the effects on gliadin peptides of the fermented food are retained. Exemplary food products include, without limitation, dairy products, e.g., milk, yoghurt, curd, cheese and cheese-based products, fermented milks, milk-based fermented products, milk-based powders, infant formulae, milk-based strained infant foods, ice cream, gelato, puddings, soups, sauces, purees, or dressings, nutritional formulas for the elderly; cereal products e.g., pablum, cereal-based strained infant foods, oatmeal, farina, semolina, polenta, pasta, biscuits, crackers, energy bars; vegetable products, e.g., purees, vegetable-based strained infant foods, pickled vegetables including cucumbers, cabbage, carrots, beans, peppers, or relishes; fruit products, e.g., fruit-based strained infant foods, tomato products, purees, sauces, pastes, ketchups, fruit purees; or a protein-based products, e.g., legumes, sausages, lunch meats, hot dogs, or pureed meats. In some embodiments the fermented food may be combined with pet foods or animal feeds.

Pharmaceutical Compositions

The compositions described herein may be combined with a pharmaceutically acceptable carrier. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

Thus, the invention also includes pharmaceutical compositions which contain, as the active ingredient, the *L. paracasei* CBA L74 or one or more metabolites produced by *L. paracasei* CBA L74 described herein, in combination with one or more pharmaceutically acceptable carriers. In some embodiments, the *L. paracasei* CBA L74 can be sterilized using conventional sterilization techniques before or after it is combined with the pharmaceutically acceptable carrier. In making the compositions of the invention, the *L. paracasei* CBA L74 or one or more metabolites produced by *L. paracasei* CBA L74, are typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. As is known in the art, the type of diluent can vary depending upon the intended route of administration. The resulting compositions can include additional agents, such as preservatives. The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary). Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

Pharmaceutically acceptable compositions for use in the present methods, including those in which *L. paracasei* CBA L74 or one or more metabolites produced by *L. paracasei* CBA L74, are entrapped in a colloid for oral delivery, can be prepared according to standard techniques. The *L. paracasei* CBA L74 or one or more metabolites produced by *L. paracasei* CBA L74, can be dried and compacted by grinding or pulverizing and inserted into a capsule for oral administration. In some embodiments, the *L. paracasei* CBA L74 or one or more metabolites produced by *L. paracasei* CBA L74, can be combined one or more excipients, for example, a disintegrant, a filler, a glidant, or a preservative. Suitable capsules include both hard shell capsules or soft-shelled capsules. Any lipid-based or polymer-based colloid may be used to form the capsule. Exemplary polymers useful for colloid preparations include gelatin, plant polysaccharides or their derivatives such as carrageenans and modified forms of starch and cellulose, e.g., hypromellose. Optionally, other ingredients may be added to the gelling agent solution, for example plasticizers such as glycerin and/or sorbitol to decrease the capsule's hardness, coloring agents, preservatives, disintegrants, lubricants and surface treatment. In some embodiments, the capsule does not include gelatin. In other embodiments, the capsule does not include plant polysaccharides or their derivatives.

Regardless of their original source or the manner in which they are obtained, the *L. paracasei* CBA L74 or one or more metabolites produced by *L. paracasei* CBA L74, can be formulated in accordance with their use. These compositions can be prepared in a manner well known in the pharmaceutical art, and can be administered by a variety of routes, depending upon whether local or systemic treatment is desired and upon the area to be treated. Administration may be oral or topical (including ophthalmic and to mucous membranes including intranasal, vaginal and rectal delivery). In some embodiments, administration can be pulmonary (e.g., by inhalation or insufflation of powders or aerosols, including by nebulizer; intratracheal, intranasal, epidermal and transdermal) or ocular. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

The compositions can be formulated in a unit dosage form, each dosage containing, for example, from about 0.005 mg to about 2000 mg of *L. paracasei* CBA L74 or one or more metabolites produced by *L. paracasei* CBA L74, per daily dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.005 mg to about 1000 mg of the *L. paracasei* CBA L74 or one or more metabolites produced by *L. paracasei* CBA L74, of the present invention.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient.

In some embodiments, tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The proportion or concentration of the compositions of the invention in a pharmaceutical composition can vary depending upon a number of factors including dosage, chemical characteristics (e.g., hydrophobicity), and the route of administration. For example, the *L. paracasei* CBA L74 or one or more metabolites produced by *L. paracasei* CBA L74, of the invention can be provided in a capsule containing from about 0.005 mg gram to about 1000 mg for oral administration.

In some embodiments, the compositions can include *L. paracasei* CBA L74 fermetates, from which all or substantially all, of the *L. paracasei* CBA L74 cells have been removed. Methods for separating cells from growth media are well known in the art and can rely upon physical methods, for example, centrifugation to produce a cell pellet and a culture supernatant, filtration, ultrafiltration, tangential flow-filtration, normal flow filtration or reverse osmosis. Alternatively or in addition, the separation method can be ligand-based and include, for example, an antibody that specifically binds to *L. paracasei* CBA L74. The antibody can be coupled to a solid support such as a magnetic bead.

The compositions include one or more *L. paracasei* CBA L74 metabolites, i.e., any substance produced by *L. paracasei* CBA L74 The metabolite may be encoded by one or more genes or it may be generated by the enzymatic activity of one or more gene products. Metabolites include, for example, small molecules, e.g., amino acids, nucleosides, nucleotides as well as larger polymeric structures such as polypeptides, carbohydrates, nucleic acids, proteoglycans and lipids. The metabolite can be a primary metabolite, e.g., a metabolite directly involved in normal cell function, or a secondary metabolite, e.g., a metabolite typically not required for fundamental cellular functions. A metabolite can also include any metabolic intermediate generated during the synthesis of a primary or secondary metabolite. Intermediates can include, but are not limited to intermediates of Embden-Meyerhof, pentose phosphate (pentose-P) pathways, Entner-Doudoroff pathway, citrate cycle, and amino acid biosynthesis.

Exemplary primary metabolites include, without limitation, alcohols, e.g., ethanol, methanol, butanol; amino acids, e.g., lysine, arginine, ornithine, histidine, citrulline, isoleucine, alanine, valine, leucine, glycine, threonine, serine, proline, phenylalanine, tyrosine, tryptophan, cysteine, cystine, methionine, glutamic acid, aspartic acid, glutamine, and asparagine; nucleotides, e.g., 5' guanylic acid; antioxidants, e.g., isoasorbic acid; organic acids, e.g., acetic acid, lactic acid, citric acid; vitamins, e.g., vitamin B12; sugars, fatty acids.

A metabolite can also be a secondary metabolite. Secondary metabolites are typically those that are not required for fundamental cellular functions. Secondary metabolites can vary widely; exemplary secondary metabolites include antibiotics, hormones, flavonoids, terpenoids, alkaloids, phenylpropanoids, phenyl derivatives, hexanol derivatives, coumarins, stilbenes, cyanohydrins, glucosinolates, sterols, and saponins.

Lactobacilli typically produce the following metabolites during the fermentation of milk products: lactic acid/lactate, acetate, ethanol, formate, acetaldehyde, α-acetolactate, acetoin, diacetyl, and 2,3 butylene glycol (butanediol) during the fermentation of milk products. Fermentation can be any process in which a microbe causes or contributes to a breakdown of a complex organic substance into simpler substances.

The *L. paracasei* CBA L74 metabolite can be contained within media, fermentates or culture supernatants. In some embodiments, the metabolite can be partially or substantially isolated from the media, fermentates or culture supernatants. Methods of isolation of metabolites will vary according to the structure and chemistry of the particular metabolite. A partially or substantially isolated metabolite will retain the functional activity, i.e., the ability to confer a therapeutic effect on an offspring when administered to the lactating mother of the offspring. Standard art-known methods can be used for isolation and characterization of *L. paracasei* CBA L74 metabolites. Exemplary methods include, for example, stability analyses, e.g., stability to heat, pH, and/or enzymatic activity; chromatographic analysis, e.g., size exclusion chromatography, high performance liquid chromatography (HPLC), gas chromatography, thin layer chromatography, ion exchange chromatography, affinity chromatography, reverse phase chromatography; mass spectrometry.

Methods of Use

The compositions and methods disclosed herein are generally and variously useful for to treat or reduce the severity of microbial infections in infants when administered to the lactating mothers of those infants. The compositions can be administered to the mother prenatally, that is before the infant is born, or postnatally, that is after the infant is born, or both prenatally, that is, before the infant is born, and postnatally, that is, after the infant is born. Subjects for whom such treatment is beneficial include normal, full-term infants as well as premature, pre-term or low birthweight infants.

The invention is not so limiting however and the methods can be used in the treatment and prevention of infections in lactating infants of any age, for example, 1, 2, 3, 4, 5, 6, 7, 8, 9, 10, 11, 12, 13, 14, 15, 20, 30 days of age; or 1, 2, 3, 4, 5, 6, 7, 8, 9, 10, 11, or 12 months of age; or 1, 2, 3, or about 4 years of age or up until the infant is weaned. The methods are applicable to both congenital infections, i.e., infections acquired in utero, and neonatal infections, i.e., infections acquired at or shortly after birth. A microbial infection can include an infection caused by a bacterium, virus, protozoa or fungus. Congenital infections are typically the result of transplacental transmission and present prenatally, intranatally or immediately post-partum. Common congenital infectious agents include *Viridans streptococci* and *S. agalactiae*. Neonatal infections generally are acquired as ascending infections from the birth canal, or via the external environment or through breast milk. Such infections present during the post-partum period e.g., within about a month after birth. Common neonatal infectious agents include for example, *Viridans streptococci, S. agalactiae* and other Group B *Streptococcus, Cronobacter sakazakii, Salmonella typhimurium, Escherichia coli, Klebsiella* spp., *Listeria monocytogenes, Streptococcus pneumoniae, Neisseria meningitidis Staphylococcus aureus, Streptococcus pyogenes, Yersinia, Shigella, Clostridium,* and *Helicobacter pylori*. In some embodiments, the infectious agent can be a virus, e.g., rotavirus, rubella, cytomegalovirus, or a herpesvirus. In some embodiments, the infectious agent can be a protozoa, e.g., *Entamoeba histolytica, Cryptosporidium* spp, *Campylobacter* spp., or *Toxoplasma* spp. In some embodiments, the infectious agent can be a fungus, e.g., *Candida* spp., e.g., *C. albicans* or *C. parapsilosis*, or *Malassezia, Zygomycetes*, or *Aspergillus*

A subject, e.g., an offspring of a lactating mother receiving a food product or pharmaceutical composition comprising *L. paracasei* CBA L74 described herein, is effectively treated whenever a clinically beneficial result ensues. This may mean, for example, a complete resolution of the symptoms associated with an infection, a decrease in the severity of the symptoms associated with an infection, or a slowing of the progression of symptoms associated with an infection. These methods can further include the steps of a) identifying a subject (e.g., a patient and, more specifically, a human patient) who has an infection; and b) providing to the lactating mother of the patient a composition comprising *L. paracasei* CBA L74 described herein, such as any fermented food product or composition comprising *L. paracasei* CBA L74 in a physiologically acceptable carrier. An amount of such a composition provided to the lactating mother that results in a complete resolution of the infant's symptoms associated with an infection, a decrease in the severity of the symptoms associated with an infection, or a slowing of the progression of symptoms associated with an infection is considered a therapeutically effective amount. The present methods may also include a monitoring step to help optimize dosing and scheduling as well as predict outcome.

The methods disclosed herein can be applied to a wide range of species, e.g., humans, non-human primates (e.g., monkeys), horses, pigs, cows or other livestock, dogs, cats or other mammals kept as pets, rats, mice, or other laboratory animals. The compositions described herein are useful in therapeutic compositions and regimens or for the manufacture of a medicament for use in treatment of conditions as described herein (e.g., a neonatal or congenital infection).

The nutritional compositions described herein can be administered orally as part of the ordinary daily diet of the pregnant or lactating mother. When formulated as pharmaceuticals, the compositions can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

Regardless of whether the compositions are formulated as food products or as pharmaceuticals, the dosage required will depend on the route of administration, the nature of the formulation, the mother's size, weight, surface area, age, and sex, other drugs being administered, and the judgment of the attending clinicians. Suitable dosages are in the range of 0.01-1,000 mg/kg. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compound selected, formulation of the excipient, and its route of administration.

Effective doses can be extrapolated from dose-response curves derived from in vitro or animal model test systems. For example, in vitro analysis of immune system functioning, e.g., cytokine production by peripheral blood mononuclear cells (PBMCs) can be a useful for assaying pro- and anti-inflammatory responses, e.g., secretion of IL-1β, IL-12, IL-4, TNF-α, or IL-10 respectively. Compositions can also be analyzed for effects in animal models, for example, survival rates in model infection systems e.g., with *C. sakazakii* or *S. typhimurium* or other indicators of immune system functioning, e.g., IgA production, cytokine production by explants of Peyer's patches, and dendritic cell and T-cell responses.

Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can also vary. Administration of the compositions can begin during pregnancy and continue after birth until the offspring is weaned. Alternatively, the administration can be discontinued after birth or the administration can begin any time after the birth of the offspring and continue until the offspring is weaned. It is also noted that the frequency of treatment can be variable. For example, the present compositions can be administered once (or twice, three times, etc.) daily, weekly, monthly. When the compositions are formulated as food product, for example, the compositions can be administered daily at every meal.

Any method known to those in the art can be used to determine if a particular response is induced. Clinical methods that can assess the degree of a particular disease state can be used to determine if a response is induced. For example, a subject can be monitored for symptomatic relief, e.g., relief from fever, colic, diarrhea, nausea, vomiting, seizures, jaundice, low blood sugar, in addition to monitoring by clinical assays, e.g., culturing for microorganisms, blood counts, cerebrospinal fluid screening, serum markers, imaging techniques, e.g., ultrasound, x-rays, and endoscopic methods.

The compositions may also be administered in conjunction with other therapeutic modalities. In some embodiments, the offspring can be treated with standard agents, for example, antibiotics, anti-inflammatory agents, anti-histamines and other dietary treatments, for example, hypoallergenic infant formulas. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. When only a single machine is illustrated, the term "machine" shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures.

EXAMPLES

Example 1: Materials and Methods

Preparation of L. paracasei CBA L74 Fermented Milk:
Substrate: 9% reconstituted skim milk powder, dextrose added at 0.25%
Substrate heat treatment: UHT—135° C. for 3 s or equivalent $F_0$
Co-Inoculum: $5\times10^6$ for Lactobacillus paracasei CBA-L74 $5\times10^4$ for Streptococcus thermophilus (as starter of the fermentation)
Fermentation Temperature: 37° C.
Fermentation time: 15 h hours
pH during fermentation: no adjustment
At the end of the fermentation pH adjustment to 6.5 with NaOH solution
Spray drying with inlet temperature 190° C. and outlet temperature 90° C.
Analysis: Cells count on the fermentate to determine Streptococcus thermophilus and Lactobacillus paracasei CBA L74
Plating:
Lactobacilli selective agar (LBS) was used for detection of Lactobacillus paracasei CBA L74. L-M17 agar was used for Streptococcus thermophilus counts. Both were incubated at 37° C. anaerobically. Plate count agar (PCA) was used for detection of contaminants and incubated at 30° C. aerobically.
Fermentation:
L. paracasei CBA L74 and S. thermophilus 1773 co-inoculum were added as fresh cultures. Fermentation was carried out for 15 hours, to a concentration of $10^8$ cfu/mL of L. paracasei CBA L74. The initial pH was 6.6. At the end of the fermentation the pH was 5.1. The pH was adjusted to 6.5 by adding 2.5N NaOH. The initial concentration of L. paracasei CBA L74 was $5\times10^6$ CFU/ml; the final concentration was more than $10^8$ CFU/ml. The initial concentration of Streptococcus thermophilus was $5\times10^4$ CFU/ml; the final concentration was $1\times10^8$ CFU/ml. The initial total bacterial count on PCA was 0 in the milk prior to inoculation and at T0 and too few colonies to count (TFTC) after the 15 hour fermentation period. was $5\times10^4$ CFU/ml; the final concentration was $1\times10^8$ CFU/ml.
Drying:
The fermentate was dried at an inlet temperature of 190° C. and an outlet temperature of 90° C. The moisture content of the powder after spray drying was 4.87%.
Preparation of L. paracasei CBA L74 Fermented Rice:
We prepared a one liter solution of 15% weight/volume of rice by combining 150 g of rice and 900 ml of water. The mixture was prepared at room temperature and mixed by shaking for several minutes at 1000-1300 rpm. The rice mixture was treated by tyndalization by heating of the mixture inside the instrument at 70° C., starvation at 70° C. per 20-30 minutes, cooling at 30-37° C., starvation at 30-37° C. per 20-30 minutes, heating at 70° C., starvation at 70° C. per 20-30 minutes, cooling at the fermentation temperature (37° C.) while shaking at 150-600 rpm.
L. paracasei CBA L74 was added from a freeze-dried sample to a final concentration of $1\times10^6$ CFU/ml. The freeze-dried sample was resuspended in water and incubated briefly at 37° C. to activate the bacteria. After the inoculation, the mixture was homogenized by shaking briefly at 300-600 rpm; during fermentation the solution was shaken at 150 rpm. Fermentation was carried out at 37° C. for 24 hours at a pO2 of <15%. Aliquots were collected at the time of inoculation (T0), at 16 hours (T16), 18 hours (T18), 21 hours (T21) and at 24 hours (T24). After fermentation, the cereal was heated to 50° C. with continuous mixing. The heated cereal was then spray dried at T $air_{in}$ 80° C., T $air_{out}$ 210° C. The final moisture content was 6%.
Samples were analyzed on Rogosa agar (+vancomycin 12 microgr./ml) (48 h at 37° C.), for quantification of the L. paracasei CBA L74), on PCA for total aerobes (24 h at 37° C.), on McConkay agar for coliformes and RCM agar for clostridia.
The results of this fermentation were as follows:
inoculum (L. paracasei CBA-174): $1\times10^6$(+/-½ log) CFU/ml (on the instrument) L. paracasei CBA L74 concentration after 24 hours of fermentation: $1\times10^8$ (+/-½ log) CFU/ml
Contaminants on PCA before inoculum: $<10^4$ CFU/ml
Contaminants on McConkay before inoculum: $<10^4$ CFU/ml
Contaminants on RCM before inoculum: <10 CFU/ml
Contaminants on PCA after inoculum: $<10^4$ CFU/ml
Contaminants on PCA after 24 hours of fermentation: $<10^4$ CFU/ml
pH before the addition of inoculum: 6 (+/-0.20)
pH at 16-18 hours: 3.70 (+/-0.20)
pH at 24 hours: 3.60 (+/-0.20).

Example 2: Effect of Maternal Administration of L. paracasei CBA L74 Fermented Rice on Survival of C. sakazakii Infected Offspring L. paracasei CBA L74 fermented rice was prepared as described in Example 1. Standard mouse food pellets (Mucedola, SLR, 4RF21 GLP Certificate) were mixed with either L. paracasei CBA L74 fermented rice or non-fermented rice such that the rice constituted 10% of the total daily diet of the mice. This amount was designed to mimic the daily amount of L. paracasei CBA L74 that an infant would receive if the fermented rice were administered directly to the infant. Pregnant CD1 mice received food pellets containing either L. paracasei CBA L74 fermented rice or non-fermented rice beginning on the 14th day of pregnancy through delivery on the 21st day of pregnancy and during lactation.

Bacterial infection of the pups with *C. sakazakii* was carried out as follows. *C. sakazakii* strain N13 was grown in M17 broth until OD600≈0.6 and resuspended in carbonate buffer (5% in water) at a concentration of $10^{10}$ CFU/100 μl. Serial dilutions were plated on LB agar to verify for inoculum concentration.

Figure 2:
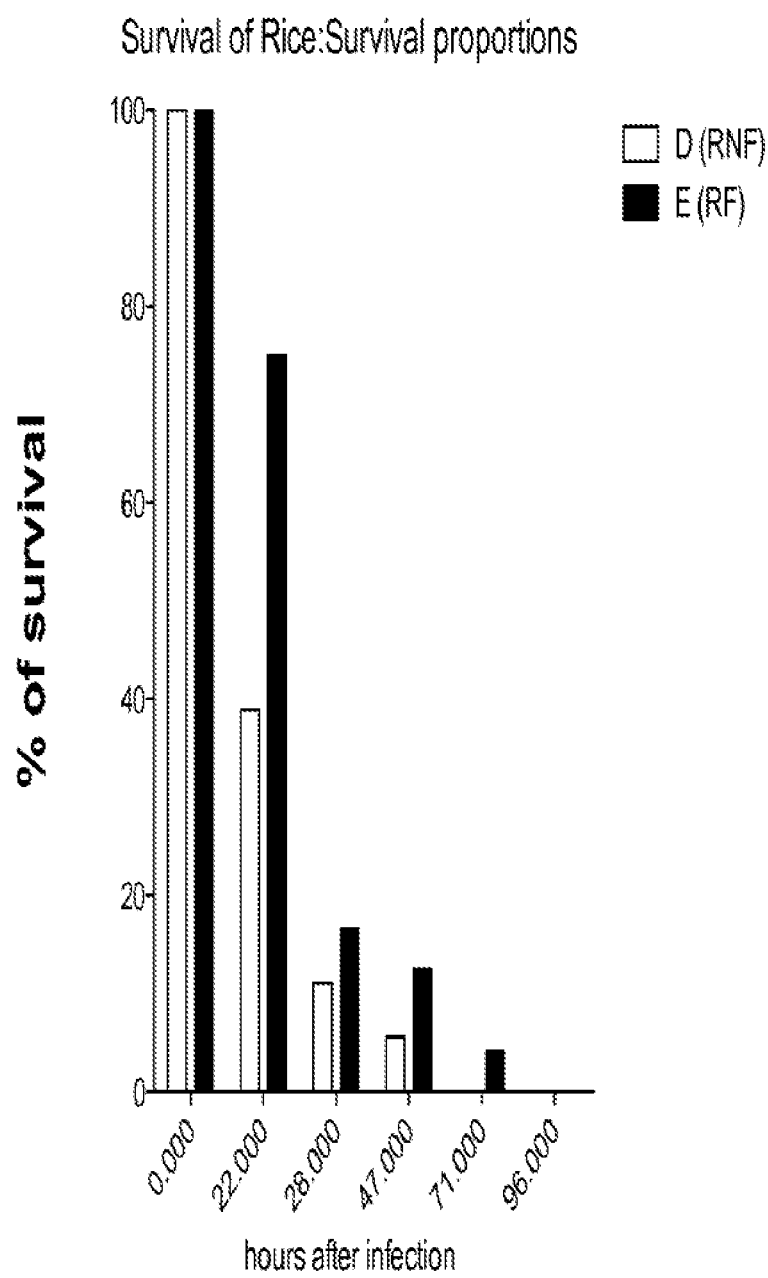
FIG. 2 is a graph depicting the results of an analysis of the effect of maternal administration of *L. paracasei*, strain CBA L74 fermented rice on the survival of *Cronobacter sakazakii* infected offspring.

The pups were dosed with 100 μl of bacterial solution (i.e., $10^{10}$ CFU) administered via oral gavage at post-natal day 3. Pups were assessed daily for survival and results presented as Kaplan-Meier survival curve. The results of this experiment are shown in FIG. 1 and FIG. 2. As shown in FIG. 2, a higher percentage of the pups from mothers who received *L. paracasei* CBA L74 fermented rice during pregnancy and lactation ("E (RF)) (solid bars) survived *C. sakazakii* infection when compared to those pups whose mothers received non-fermented rice ("D(RNF)) (white bars).

Example 3: Effect of Maternal Administration of *L. paracasei* CBA L74 Fermented Milk on Survival of *S. typhimurium* FB62 Infected Offspring

*L. paracasei* CBA L74 fermented milk was prepared as described in Example 1. Standard mouse food pellets (Mucedola, SLR, 4RF21 GLP Certificate) were mixed with either *L. paracasei* CBA L74 fermented milk or non-fermented milk such that the milk constituted 5% of the total daily diet of the mice. This amount was designed to mimic the daily amount of *L. paracasei* CBA L74 that an infant would receive if the fermented milk were administered directly to the infant. Pregnant CD1 mice received food pellets containing either *L. paracasei* CBA L74 fermented milk or non-fermented milk beginning on the 14th day of pregnancy through delivery on the 21st day of pregnancy and during lactation.

Bacterial infection of the pups with *S. typhimurium* FB62 was carried out as follows. *S. typhimurium* FB62 was grown in LB until $OD_{600}$≈0.6 and resuspended in carbonate buffer (5% in water) at a concentration of $10^8$ CFU/100 μl. Serial dilutions were plated on LB agar to verify for inoculum concentration.

Figure 3:
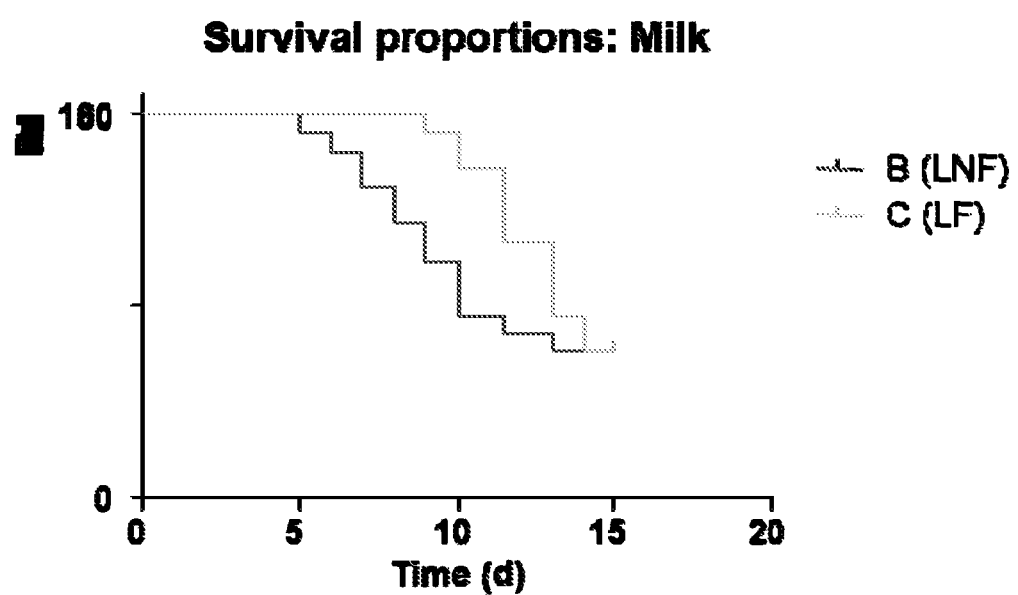
FIG. 3 is a graph depicting the results of an analysis of the effect of maternal administration of *L. paracasei* CBA L74 fermented milk on survival of *Salmonella typhimurium* FB62 infected offspring.

The pups were dosed with 100 μl of bacterial solution administered via oral gavage at post-natal day 15. Pups were assessed daily for survival and results presented as Kaplan-Meier survival curve. The results of this experiment are shown in FIG. 3. As shown in FIG. 3, a higher percentage of the pups from mothers who received *L. paracasei* CBA L74 fermented milk during pregnancy and lactation ("C (LF)") survived *S. typhimurium* FB62 infection when compared to those pups whose mothers received non-fermented milk ("B(LNF)").

What is claimed is:

1. A method of treating a microbial infection or reducing the severity of a microbial infection in an infant of a lactating mother, the method comprising administering to the mother an effective amount of a composition comprising probiotic bacterium *Lactobacillus paracasei* CBA L74, International Depository Accession Number LMG P-24778, wherein the probiotic bacterium has been rendered non-replicating, the concentration of the probiotic bacterium in the composition is at least $1\times10^7$ colony forming units (CFU) per gram as calculated prior to rendering the probiotic bacterium non-replicating, and the microbe causing the infection being treated comprises at least one of *Salmonella typhimurium* and *Cronobacter sakazakii*.

2. The method of claim 1, further comprising identifying an infant in need of treatment.

3. The method of claim 1, wherein the microbe causing the infection being treated comprises *Salmonella typhimurium* FB62.

4. The method of claim 1, wherein the microbe causing the infection being treated comprises *Cronobacter sakazakii*.

5. The method of claim 1, wherein the composition is administered until a symptom of the infection improves.

6. The method of claim 1, wherein the composition comprises a food product or a pharmaceutical carrier.

7. The method of claim 1, wherein the concentration of the probiotic bacterium in the composition is between $1\times10^7$ and $1\times10^{12}$ colony forming units (CFU) per gram.

8. A method of treating a microbial infection or reducing the severity of a microbial infection in an infant of a lactating mother, the method comprising administering to the mother an effective amount of a composition comprising a culture supernatant of probiotic bacterium *Lactobacillus paracasei* CBA L74 cells, International Depository Accession Number LMG P-24778, wherein the composition is administered in an amount of from 0.01 to 1,000 mg per kg based on the weight of the mother, and the microbe causing the infection being treated comprises at least one of *Salmonella typhimurium* and *Cronobacter sakazakii*.

9. The method of claim 8, further comprising identifying an infant in need of treatment.

10. The method of claim 8, wherein the microbe causing the infection being treated comprises *Salmonella typhimurium* FB62.

11. The method of claim 8, wherein the microbe causing the infection being treated comprises *Cronobacter sakazakii*.

12. The method of claim 8, wherein the composition is administered until a symptom of the infection improves.

13. The method of claim 8, wherein any probiotic bacterium *Lactobacillus paracasei* CBA L74 cells in the culture supernatant have been rendered non-replicating.

14. The method of claim 8, wherein the probiotic bacterium *Lactobacillus paracasei* CBA L74 cells have been removed from the culture supernatant.

15. The method of claim 8, wherein the composition comprises a food product or a pharmaceutical carrier.

* * * * *